United States Patent [19]

Nederlof

[11] Patent Number: 5,660,722
[45] Date of Patent: Aug. 26, 1997

[54] HEMO(DIA)FILTRATION APPARATUS AND FILTRATE FLOW REGULATOR

[75] Inventor: Bernd Nederlof, St. Wendel, Germany

[73] Assignee: Fresenius AG, Bad Homburg, Germany

[21] Appl. No.: 501,210

[22] Filed: Jul. 11, 1995

[30] Foreign Application Priority Data

Jul. 13, 1994 [DE] Germany ............. 44 24 693.5

[51] Int. Cl.$^6$ ................. B01D 61/32; B01D 61/58
[52] U.S. Cl. .......... 210/90; 210/321.65; 210/335; 210/434; 210/641; 210/644; 210/646
[58] Field of Search ............ 210/90, 137, 195.2, 210/321.72, 321.75, 416.1, 433.1, 434, 637, 641, 644, 645, 646, 335; 604/4–6

[56] References Cited

U.S. PATENT DOCUMENTS

| | | | |
|---|---|---|---|
| 2,140,341 | 12/1938 | Wallach et al. | 210/644 |
| 2,247,143 | 6/1941 | Bailey | 210/644 |
| 2,571,210 | 10/1951 | Craver | 210/644 |
| 2,683,117 | 7/1954 | Rosenak et al. | 210/335 |
| 3,799,873 | 3/1974 | Brown | 210/641 |
| 4,338,190 | 7/1982 | Kraus et al. | 210/195.2 |
| 4,702,829 | 10/1987 | Polaschegg et al. | 210/335 |
| 4,834,888 | 5/1989 | Polaschegg | 210/646 |
| 4,886,602 | 12/1989 | Kuehne et al. | 210/644 |
| 4,997,510 | 3/1991 | Polaschegg | 210/646 |
| 5,431,811 | 7/1995 | Tusini et al. | 210/195.2 |

*Primary Examiner*—Joseph W. Drodge
*Attorney, Agent, or Firm*—Townsend and Townsend and Crew LLP

[57] ABSTRACT

Described is a hemo(dia)filtration apparatus (10) with two blood filters (60) and (12) connected in series and a sterile filter (38) connected upstream thereof. The first chambers (64) and (14) and the second chambers (68) and (16) of both blood filters (60) and (12) are connected to one another, respectively, by connecting lines (72) and (74). A means (76) is arranged in one of the connecting lines (72) and (74), which generates a positive transmembrane pressure in the direction of the blood path in one of the blood filters (60, 12) and a negative transmembrane pressure in the direction of the blood path (80) in the other blood filter (12, 60). This eliminates a costly substitute line with additional devices arranged therein, since the dialyzer fluid is passed as a substitute solution through the membrane of the one blood filter directly into the blood. Furthermore, with the use of suitable devices it is possible to precisely determine and individually adjust the filtrate and substitute flows.

13 Claims, 3 Drawing Sheets

HEMO(DIA)FILTRATION APPARATUS AND FILTRATE FLOW REGULATOR

BACKGROUND OF THE INVENTION

The invention relates to a hemo(dia)filtration apparatus comprising a blood filter divided by a membrane into two chambers, in which the first chamber is connected into a dialyzer fluid path and the second chamber is connected into a blood path, in which the dialyzer fluid path is a supply line extending from a means for preparing the dialyzer to a blood filter and into which a first balance chamber is connected, and which has a discharge line extending from the blood filter to a drain and into which a second balance chamber is connected, a pump for conveying dialyzer fluid within a closed dialyzer fluid system, a bypass line connecting the supply line with the discharge line of the dialyzer fluid path, in which a bypass valve is arranged, an ultrafiltration device, a first sterile filter incorporated in the supply line between the first balance chamber and the blood filter which is divided by a germ-repelling membrane into a first and a second chamber, and a second sterile filter divided by a germ-repelling membrane into a first and a second chamber.

During hemofiltration blood is conducted past the membrane of a hemofilter, in which part of the serum is withdrawn via the membrane and replaced by a sterile substitution fluid added to the extracorporeal blood path either upstream (predilution) or downstream (post dilution) of the blood filter. In addition, in the hemodiafiltration, the usual hemodialysis is carried out, i.e. dialyzer fluid is conducted past the membrane of the hemodialyzer so that across the membrane an exchange of urophanic substances can take place.

Dialyzer fluid may be produced on-line from fresh water and an electrolyte concentrate and the substitution fluid may be produced on-line from the dialyzer fluid. Though the electrolyte concentrate is as a rule inherently sterile and fresh water is generally germ-free, there is no certainty that the dialyzer fluid produced on-line is absolutely sterile and free of pyrogens, which is why the dialyzer fluid is rendered sterile and pyrogen-free for producing the substitute fluid. To achieve this, dialyzer fluid is removed via a line upstream of the blood filter, into which line at least one sterile filter is connected.

An apparatus of the this type is known, for example, from DE 34 44 671A.

Due to a so-called "dead-end" arrangement of the sterile filter in the substitute line, the above mentioned device has the drawback that in the course of time particles and other substances, e.g. imported germs and pyrogens, accumulate in front of the sterile filter membrane. This is especially dangerous if as a result of a rupture these substances can suddenly be carried into the sterile region, thereby contaminating the substitution fluid.

Further risks of contamination exist in the form of the substitute line and its additional components, such as, for example, substitute pump and ventilation means and, finally, the design of the substitute line itself is constructionally complex due to these added components, and thus very costly.

Further, it is known from the article by v. Albertini, et at., "Serial and parallel pairs of dialyzers for high-efficiency treatment", in Kidney International 31(1), 1987, page 247, to arrange serially or in parallel two blood filters to enhance the purifying action. A means for precisely regulating and monitoring the filtrate and substitute flow is not mentioned in this publication.

Operating these apparatuses both safely and efficiently requires costly and complex devices for regulating and monitoring the ratio of substituate and filtration. Moreover, measuring the permeability of the blood filter membrane is not possible without great expenditure and added structural complexity.

Thus, the object of the present invention is, based on a hemo(dia)filtration apparatus of the aforementioned kind, to provide a simpler, more efficient and safer hemo(dia) filtration apparatus, in which clogging of the sterile filter with germs or pyrogens is largely eliminated, in which the ratio of filtrate and substituate is regulated and monitored in a simple and safe manner, and in which the permeability of the blood filter membrane may be measured in a safe, simple manner.

SUMMARY OF THE INVENTION

The object of the present invention is achieved in that the second sterile filter also functions as another blood filter arranged in the supply line between the first sterile filter and the first blood filter, in that the first chamber of the second blood filter is connected into the dialyzer fluid path and the second chamber is connected into the blood path, in that the first chamber of the second blood filter is connected by a connecting line to the first chamber of the first blood filter and the second chamber of the second blood filter is connected by a second connecting line to the second chamber of the first blood filter, and in that at least one pump for generating a pressure differential between the blood filters is arranged in one of the connecting lines in such a way that in the one blood filter a positive transmembrane pressure is generated in the direction of the blood path, and in the other blood filter a negative transmembrane pressure is generated in the direction of the blood path.

The arrangement of a second blood filter according to the present invention allows for a more efficient hemodialysis on the one hand, and on the other hand eliminates the need for a costly substituate line equipped with additional devices which normally feed the substituate into the blood path, since the dialyzer fluid is passed as a substituate solution through the membrane of the one blood filter directly into the blood. Thus, contamination of the substituate while passing through the substituate line is no longer possible. In addition, it is possible to precisely determine and individually adjust the filtrate and substituate flow by means of suitable devices which, for example, determine and regulate the pressure differential between the blood filters. Further, it is possible to simply and efficiently monitor the membranes of both blood filters by intermittently switching the pressure differential between the blood filters by means of a blood leak detector.

In a particularly advantageous embodiment of the present invention, the first sterile filter is connected into the supply line and the first chamber of the first sterile filter is switched intermittently during flow through. In addition, the first chamber of the first sterile filter is connected to the bypass line which leads to the discharge line.

This arrangement of the first sterile filter results in a sterilizing filtration action of the dialyzer fluid, such that a completely sterile dialyzer fluid is conveyed to connecting blood filters. By opening the bypass valve, which may be open during treatment and as the entire apparatus is being flushed, the dialyzer fluid drains out of the first chamber of the sterile filter carrying along any pyrogens and particles on the membrane into the discharge line and from there into the drain. It is thereby feasible to flush the membrane at predetermined intervals, thereby reliably preventing accumulation of germs and pyrogens on the membrane. Clogging of the membrane which results in an elevated transmembrane pressure is a principle cause of ruptures, hence, the likelihood of a rupture is lessened thereby, and this ensures the sterility of the dialyzer fluid and improves the safety of the hemo(dia)filtration apparatus.

According to the present invention, the means for generating a pressure differential between the blood filters is equipped with at least one pump. First, this allows precise regulation of the substituate flow and of the filtrate flow through the blood filter membranes, and secondly, it allows the filtrate and substituate flows to be reversed. By intermittently switching the filtrate and substituate flow, it is further possible to monitor the sealing of the blood filter membranes in an extremely simple and efficient manner, e.g. by means of a blood leak detector.

An advantageous development of the present invention provides for a second bypass line leading from the connecting line between the first chambers of the blood filter to the discharge line of the dialyzer fluid path. A first pump is then connected into the first connecting line between the first chambers of the blood filter, downstream of the junction of said bypass line with the connecting line and upstream of the first blood filter, and a second pump is connected into the discharge line downstream of the first blood filter and upstream of the junction of the second bypass line. This permits an uninterrupted flow of dialyzer fluid through the dialyzer fluid path and through the second blood filter. If required, it is also feasible to connect the first blood filter into the dialyzer fluid path and to generate a pressure differential between the first and second blood filters by varying the pumping rates of both pumps.

On the whole, an efficient and simple hemo(dia)filtration apparatus is achieved which offers two-fold protection against blood contamination, in that as a substituate solution the dialyzer fluid is filtered twice as it passes into the blood, and in which contamination of the substituate solution is not possible, since it is passed directly into the blood and no longer conveyed into the blood path through a substituate line with additional devices arranged therein. Furthermore, by at least partially flushing the membrane of the first sterile filter and by continuously flushing the membranes of both blood filters, an accumulation of germs and pyrogens on these membranes is prevented, thereby reducing considerably the danger of a rupture proximate said membranes. Still further, the intact condition of these membranes can be tested in a simple and effective manner, thus resulting in a hemo(dia)filtration apparatus with a high degree of safety, and the ratio of substituate and filtrate can be individually adjusted.

BRIEF DESCRIPTION OF THE DRAWINGS

Further details, features and advantages of the present invention are explained with the aid of the following description of four embodiments with reference to the drawings, in which:

In FIG. 1 the numeral 10 denotes a diafiltration apparatus which comprises a first blood filter 12 which is divided by a membrane 18 into a first chamber 14 through which the dialyzer fluid flows and a second chamber 16 through which blood flows, and further a second blood filter 60 divided by a membrane 62 into a first chamber 64 through which dialyzer fluid flows and a second chamber 68 through which blood flows.

DESCRIPTION OF THE PREFERRED EMBODIMENT

Figure 1:
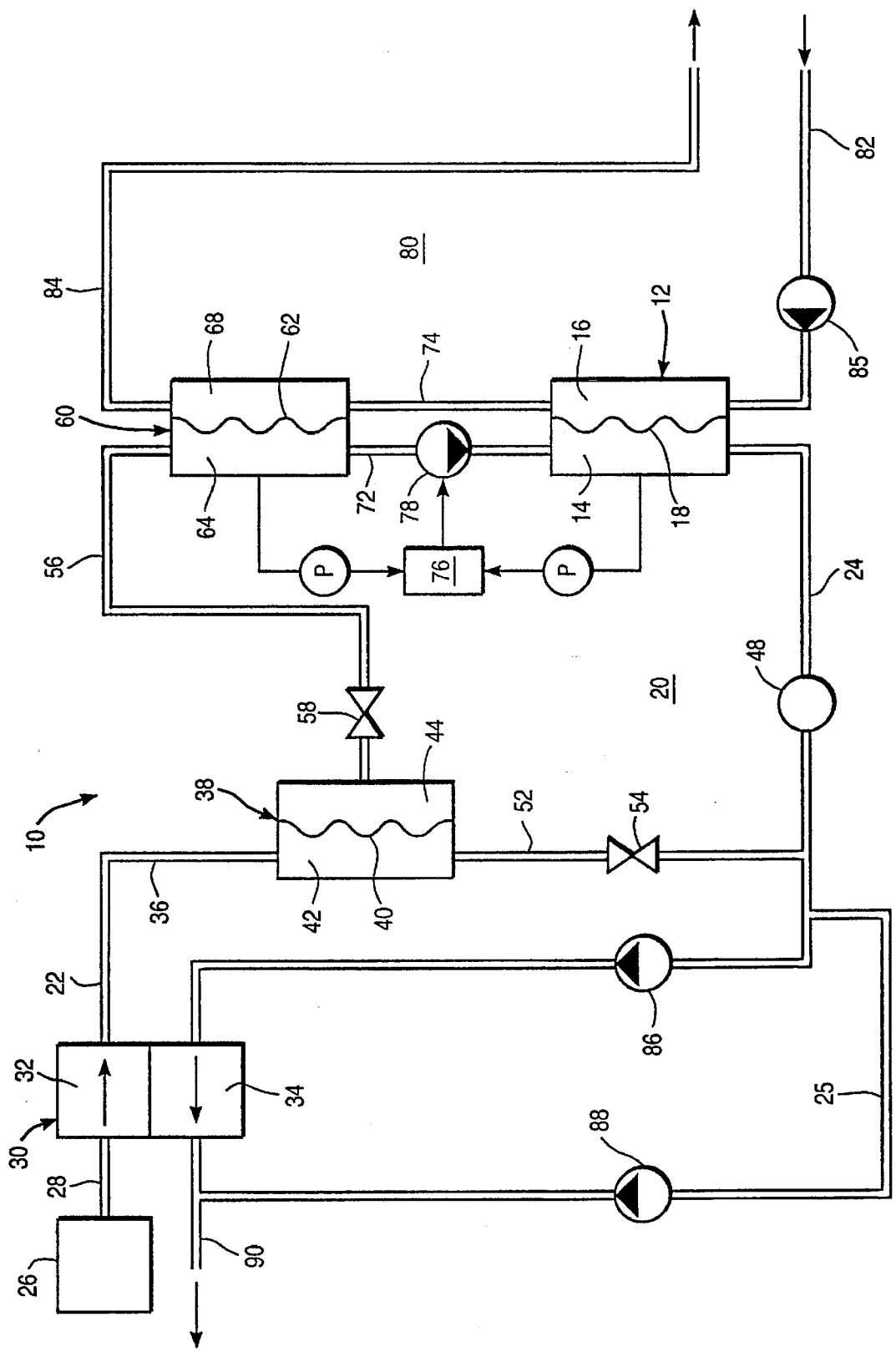
FIG. 1 is a schematic representation of a first embodiment of the filtrate flow regulator.

The first chamber 14 of the first blood filter 12 and the first chamber 64 of the second blood filter 60 are connected into a dialyzer fluid path 20, consisting of a supply line 22 and a discharge line 24, and the second chamber 16 of the first blood filter 12 and the second chamber 68 of the second blood filter 60 are connected into a blood path 80.

The supply line 22 consists of a first supply line section 28, a second section 36 and a third section 56, and it connects a dialyzer fluid source 26 to the first chamber 64 of the second blood filter 60.

The first supply line section 28 connects the dialyzer fluid source 26 to the first chamber 32 of a balancing unit 30. The first chamber 32 of the balancing unit 30 is connected to the first chamber 42 of a sterile filter 38 by way of the second supply line section 36. Sterile filter 38 is subdivided by a membrane 40 into a first chamber 42 and a second chamber 44. The outlet of the first chamber 42 of sterile filter 38 is connected to a bypass line 52, into which a bypass valve 54 is connected and which is connected to discharge line 24.

The third supply section 56 branches off the second chamber 44 of sterile filter 38 and is connected to the first chamber 64 of the second blood filter 60. A valve 58 is connected into the third supply line section 56. The first chamber 64 of the second blood filter 60 is connected to the first chamber 14 of the first blood filter 12 by way of the first connecting line 72 and the second chamber 68 of the second blood filter 60 is connected to the second chamber 16 of the first blood filter 12 by way of the second connecting line 74.

A non-occluding pump 78 is connected into the first connecting line 72 between the first chamber 64 of the second blood filter 60 and the first chamber 14 of the first blood filter 12.

Discharge line 24 leads from the outlet of the first chamber 14 of the first blood filter 12 to the second balance chamber 34 of the balancing unit 30. A blood leak detector 48 and a dialyzer fluid pump 86 are connected into discharge line 24, further an ultrafiltrate line 25 into which an ultrafiltration pump 88 is connected, branches off discharge line 24. The ultrafiltrate line 25 leads to a drain 90 to which the outlet of the second balance chamber 34 of the balancing unit 30 is attached.

The second chamber 16 of the first blood filter 12 and the second chamber 68 of the second blood filter 60 are connected into the blood path 80 in such a way that a blood supply line 82 originating from the patient is connected to the entry of the first chamber 16, the outlet of the first chamber 16 of the first blood filter 12 is connected via the second connecting line 74 to the entry of the second chamber 68 of the second blood filter 60, and a blood discharge line 84 is attached to the outlet of the second chamber 68 of the second blood filter 60. Said blood discharge line 84 transports the blood back to the patient.

Fresh dialyzer fluid is conveyed from the dialyzer fluid source 26 through the first supply line section 28 of the first chamber 32 of the balancing unit 30. Said first balance chamber 32 is linked to the supply line 22 of the dialyzer fluid path 20 in such a way that the fresh dialyzer fluid is conducted from the first balance chamber 32 through the second supply line section 36, the sterile filter 38 and the third supply section 56 to the first chamber 64 of the second blood filter 60. From this point it is conducted through the first connecting line 72 to the first chamber 14 of the first blood filter 12. As it flows through membrane 40 of sterile filter 38 the dialyzer fluid undergoes a sterilizing filtration action, so that fully sterilized dialyzer fluid is directed into the first chamber 64 of the second blood filter 60. The outlet of the first chamber 14 of the first blood filter 12 is linked to the discharge line 24 which leads to the second balance chamber 34 of the balancing unit 30. A dialyzer fluid pump 86 is arranged in said discharge line 24, which conveys the dialyzer fluid into the dialyzer fluid path 20 of the first balance chamber 32 to the second balance chamber 34 of the balancing unit 30. The balancing unit 30 is designed in such a way that a quantity of used dialyzer fluid flowing through the second balance chamber 34 into drain 90 is replaced by an equal amount of fresh dialyzer fluid that is conveyed through the first balance chamber 32 into supply line 22.

Germs and pyrogens transported in the fresh dialyzer fluid into supply line 22 are filtered out by membrane 40 of sterile filter 38 and adhere to same. Opening bypass valve 54 in bypass line 52 which forms a link between the first chamber 42 and discharge line 24, causes the first chamber 42 to be flushed with dialyzer fluid. This causes particles, germs and pyrogens that have accumulated on the membrane 40 to be carried away by the dialyzer fluid flowing past said membrane and to be flushed through the second balance chamber 34 and into drain 90 by way of bypass line 52 and discharge line 24. This permits effective flushing of membrane 40 of sterile filter 38, thereby considerably reducing the danger of rupture and ensuring sterility of the dialyzer fluid, which results in an apparatus with a high degree of operating safety.

Further, an ultrafiltrate line 25 branches off the discharge line 24, which also leads to drain 90 and into which an ultrafiltrate pump 88 is connected. By activating the ultrafiltrate pump 88 additional fluid can be removed from the hydraulic closed dialyzer fluid path, which is then drawn through membrane 18 of the first blood filter 12 and/or through membrane 62 of the second blood filter 60 from the blood flowing through the second chamber 16 of the first blood filter 12 and the second chamber 68 of the second blood filter 60.

The substituate solution consists of fresh dialyzer fluid that has been filtered through sterile filter 38 and is conducted in the present embodiment via membrane 62 of the second blood filter 60 into the blood. Pump 78 in the first connecting line 72 between the first chamber 64 of the second blood filter 60 and the first blood chamber 14 of the first blood filter 12, is operated with respect to its direction and rate of delivery in such a way that in the first chamber 64 of the second blood filter 60 a positive transmembrane pressure is generated in the direction of blood path 80, and in the first chamber 14 of the first blood filter 12 a negative transmembrane pressure is generated in the direction of blood path 80. In this way the dialyzer fluid is filtered as substituate into the blood through membrane 62 of the second blood filter 60, and fluid is drawn through membrane 18 of the first blood filter 12 out of the blood flowing into the second chamber 16 into the first chamber 14. Both fluid quantities are equal due to the closed circuit within the balance chamber system.

By use of a means 76 for monitoring this pressure differential it is possible to precisely determine the substituate flow through membrane 62 of the second blood filter 60 and the filtrate flow through membrane 18 of the first blood filter 12, and to thereby individually adjust substituate and filtrate flow at pump 78 for regulating said pressure differential. Means 76 is equipped with pressure sensors on blood filters 12 and 30, respectively, whose pressure readings are used continuously for determining the respective filtrate flows through membranes 18 and 62. It is then possible to determine the filtrate flow at a specific pressure and known fluid rate by referring to known characteristic data (permeability, ultra filtration rate, etc.).

Such an arrangement yields two-fold protection against blood contamination; since the dialyzer fluid as a substituate solution is filtered twice before passing into the blood. Moreover, contamination of the substituate solution is not possible, in that it is passed directly into the blood and no longer conveyed into the blood path through a substituate line with additional devices arranged therein. Furthermore, at least partially flushing membrane 40 of sterile filter 38 and continuously flushing membranes 62 and 18 of both the second and the first blood filters 60 and 12, prevents an accumulation of germs and pyrogens on these membranes, thereby reducing considerably the danger of a rupture proximate any of these membranes. This ensures a continuous, absolutely sterile flow of substituate solution to the patient. Still further, with the use of blood leak detector 48 it is possible to effectively monitor membrane 18 for leaks.

The arrangement of pump 78 in the first connecting line 72 first of all permits careful regulation of the substituate flow through membrane 62 of the second blood filter 60 and of the filtrate flow through membrane 18 of the first blood filter 12 using means 76 for regulating the pressure differential. Secondly, it is possible to reverse the flow of substituate and filtrate such that the substituate is then conveyed through membrane 18 of the first blood filter 12 into the blood, and fluid is drawn out of the blood through membrane 62 of the second blood filter 60. By intermittently switching the filtrate and substituate flows it is possible via blood leak detector 48 to simply and efficiently monitor the seal of membrane 18 of the first blood filter 12 and the seal of membrane 62 of the second blood filter 60.

Figure 2:
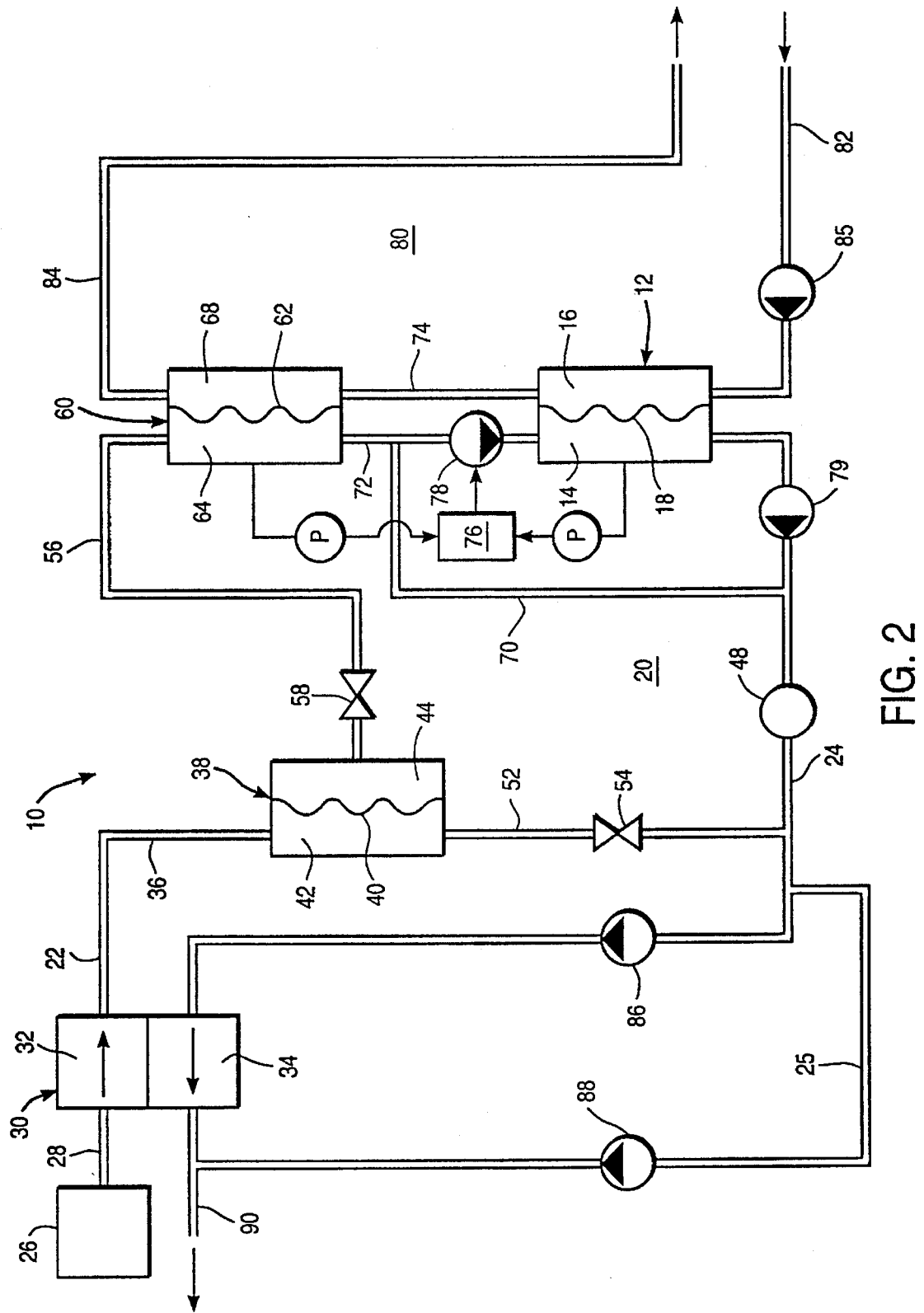
FIG. 2 is a schematic representation of a second embodiment of the present invention.

FIG. 2 shows a second embodiment of hemo(dia)filtration apparatus 10 according to the present invention, which is essentially identical to the embodiment of FIG. 1, such that identical parts are labelled with identical reference numerals and a further detailed description is not necessary.

In this second embodiment the means for generating a pressure difference between blood filters 12 and 60 is modified to the extent that a second bypass line 70 leads from the first connecting line 72 between the first chamber 64 of the second blood filter 60 and pump 78 to discharge line 24 of the dialyzer fluid path 20. Moreover, a second pump 79 is connected into discharge line 24 between the first chamber 14 of the first blood filter 12 and the junction of the second bypass line 70. In contrast to the first embodiment of the present invention both pumps 78 and 79 may be occluding pumps.

In this embodiment an uninterrupted flow of dialyzer fluid through the dialyzer fluid path 20 and the second blood filter 60 is possible, when the usual hemodialysis is to be carried out. If hemodiafiltration is to be carried out, switching on pumps 78 and 79 with different respective pumping rates generates a pressure differential between the first blood filter 12 and the second blood filter 60, thus enabling hemodiafiltration to be carried out in the manner described in detail with reference to the foregoing embodiments.

Figure 3:
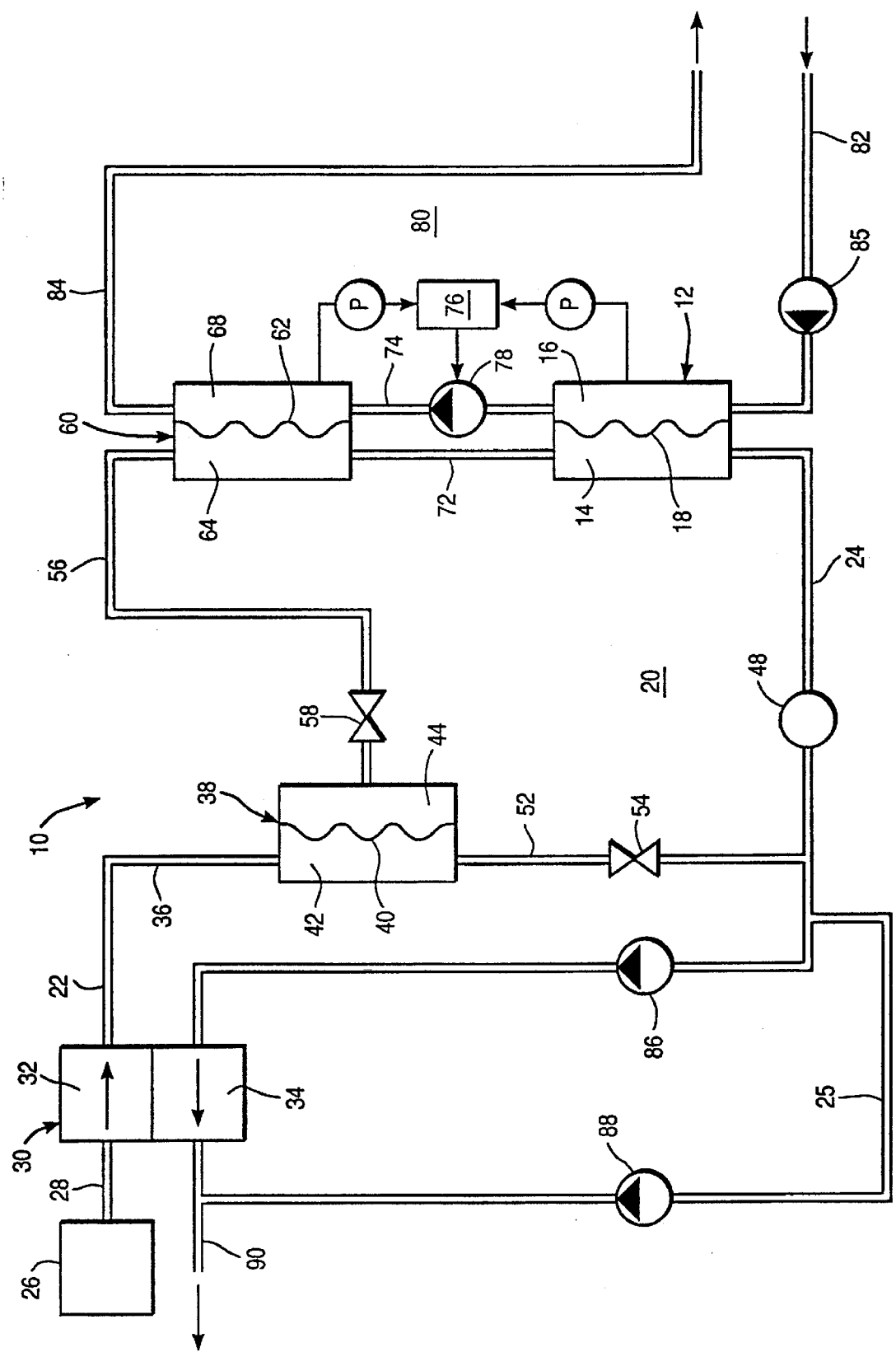
FIG. 3 is a schematic representation of a third embodiment of the present invention.

FIG. 3 shows a third embodiment of hemo(dia)filtration apparatus 10 according to the present invention. This embodiment is in large part also identical to the embodiment of FIG. 1, such that identical parts are labelled with identical reference numerals and a further detailed description is not necessary.

Contrary to the embodiment of FIG. 1 the means for generating a pressure differential between blood filter 12 and second blood filter 60 is equipped with a pump 78 which is connected into the first connecting line 74 between second chamber 16 of the first blood filter 12 and second chamber 68 of the second blood filter 60.

Pump 78 is advantageously coupled as a regulator to an arterial blood pump 85 which is normally arranged in blood path 80. Here, the delivery rate of pump 78 can be changed relative to the delivery rate of arterial blood pump 85. If a standard hemodialysis is to be carried out, the delivery rate of pump 78 is set to the delivery rate of arterial blood pump 85. If, on the other hand, a hemodiafiltration is to be carried out, the delivery rate of pump 78 can be set higher or lower than the delivery rate of arterial pump 85, depending on through which blood filter the filtrate or substituate flow is conveyed. Moreover, it is possible through intermittent switching to check the intact condition of the membranes using blood leak detector 48.

What is claimed is:

1. A hemo(dia)filtration apparatus comprising a first blood filter divided by a membrane into a first chamber and a second chamber, in which the first chamber is connected into a dialyzing fluid path and the second chamber is connected into a blood path; the dialyzing fluid path defining a closed loop between a dialyzing fluid source and a drain and including a supply line extending from the dialyzing fluid source toward the first blood filter and into which a first balance chamber is connected, the dialyzing fluid path further including a discharge line extending from the first blood filter to the drain and into which a second balance chamber is connected; a dialyzing pump for conveying dialyzing fluid along the dialyzing fluid path; a bypass line connecting the supply line to the discharge line of the dialyzing fluid path, wherein a bypass valve is arranged along the bypass line; an ultrafiltration pump in fluid communication with the discharge line; a first sterile filter incorporated in the supply line between the first balance chamber and the blood filter, the first sterile filter being divided by a germ-repelling membrane into a first and a second chamber; and a second sterile filter divided by a germ-repelling membrane into a first and a second chamber;

the second sterile filter being a second blood filter arranged in the supply line between the first sterile filter and the first blood filter, the first chamber of the second blood filter being connected into the dialyzing fluid path and the second chamber being connected into the blood path, the first chamber of the second blood filter being connected via a first connecting line to the first chamber of the first blood filter and the second chamber of the second blood filter being connected via a second connecting line to the second chamber of the first blood filter; and a first pump for generating a transmembrane pressure differential across the membranes of the first and second blood filters; the first transmembrane pressure differential pump being disposed along one of the connecting lines between the blood filters in such a way that in one of the blood filters positive transmembrane pressure is generated so as to draw fluid from the dialyzing fluid path, through the membrane, and into the blood path and in the other blood filter negative transmembrane pressure is generated so as to draw fluid from the blood path, through the membrane, and into the dialyzing fluid path.

2. Hemo(dia)filtration apparatus according to claim 1, wherein the bypass line is connected to the supply line at the first chamber of the first sterile filter so that the first sterile filter can be flushed at least intermittently during hemo(dia) filtration.

3. Hemo(dia)filtration apparatus according to claim 1, wherein a shutoff device is connected into the supply line downstream of the first sterile filter.

4. Hemo(dia)filtration apparatus according to claim 1, wherein the first transmembrane pressure differential pump is connected into the first connecting line between the first chamber of the first blood filter and the first chamber of the second blood filter, and wherein a second bypass line leads from the first connecting line between the second blood filter and the first transmembrane pressure differential pump to the discharge line of the dialyzer fluid path.

5. Hemo(dia)filtration apparatus according to claim 4, wherein a second transmembrane pressure differential pump is connected into the discharge line between the first blood filter and the junction of the second bypass line.

6. Hemo(dia)filtration apparatus according to claim 1, wherein the first transmembrane pressure differential pump is connected into the second connecting line between the second chamber of the first blood filter and the second chamber of the second blood filter.

7. Hemo(dia)filtration apparatus according to one of claims 1, 2, 3, 4, 5 or 6 wherein a pumping rate and direction of pumping of the first transmembrane pressure pump can be adjusted in such a way that a positive transmembrane pressure is generated in the first blood filter, and a negative transmembrane pressure is generated in the second blood filter.

8. Hemo(dia)filtration apparatus according to claim 1, further comprising means for monitoring a pressure differential between the first blood filter and the second blood filter.

9. Hemo(dia)filtration apparatus according to claim 1, further comprising means for regulating a pressure differential between the first blood filter and the second blood filter.

10. A hemo(dia)filtration apparatus comprising a first blood filter divided by a membrane into two chambers, in which the first chamber is connected into a dialyzing fluid path and the second chamber is connected into a blood path dialyzing fluid path comprising a supply line extending from a means for preparing the dialyzing fluid to a blood filter and comprising a first balance chamber, and said dialyzing fluid path comprising a discharge line extending from said first blood filter to a drain and comprising a second balance chamber; a first pump for conveying dialyzing fluid within a closed loop; a bypass line connecting the supply line to the discharge line of the dialyzing fluid path, in which a bypass valve is arranged; an ultrafiltration device; a first sterile filter incorporated in the supply line between the first balance chamber and the blood filter is divided by a germ-repelling membrane into a first and a second chamber; and a second sterile filter being divided by a germ-repelling membrane into a first and a second chamber; wherein said second sterile filter is also a second blood filter (60) arranged in the supply line (22) between first filter (38) and first blood filter (12), the first chamber (64) of said second blood filter (60) is connected into the dialyzing fluid path (20) and the second chamber (68) is connected into the blood path (80), said first chamber (64) of said second blood filter (60) is connected via a first connecting line (72) to the first chamber (14) of the first blood filter (12) and the second chamber (68) of the second blood filter (60) is connected via a second connecting line (74) to the second chamber (16) of the first blood filter (12), and at least one second pump (78) for generating a transmembrane pressure difference between said blood filters is arranged in one of the connecting lines (72, 74) between the blood filters (60, 12) in such a way that in one blood filter (60, 12) a positive transmembrane pressure is generated in the direction to the blood path (80) and in the other blood filter (12, 60) a negative transmembrane pressure is generated in the direction to said blood path (80).

11. A hemo(dia) filtration apparatus comprising:

a blood path including:
- a first blood filter adapted to receive a blood flow from a patient, the first blood filter having a membrane; and
- a second blood filter disposed in the blood flow from the first blood filter, the second blood filter having a membrane;

a dialyzing fluid path including:
- a first chamber of a balance unit, the first chamber capable of receiving a flow of dialyzing fluid from a dialyzing fluid source;
- a filter to sterilize the flow of dialyzing fluid from the dialyzing fluid source, the sterilizing filter having a membrane which prevents passage of germs;
- the second blood filter being disposed in the flow of dialyzing fluid from the sterile filter, the membrane of the second filter being disposed between the dialyzing fluid flow and the blood flow;
- the first blood filter being disposed in the flow of dialyzing fluid from the second blood filter, the membrane of the first filter being disposed between the dialyzing fluid flow and the blood flow; and
- a second chamber of the balance unit disposed in the flow of dialyzing fluid from the second blood filter, the balance unit conveying an equal flow of dialyzing fluid through the first and second chambers; and a pump disposed between the first blood filter and the second blood filter along an element selected from the group consisting of the blood path and the dialyzing fluid path so as to generate higher pressure in the blood flow than in the dialyzing fluid flow across the membrane of one of the first blood filter and the second blood filter, and so as to generate higher pressure in the dialyzing fluid flow than in the blood flow across the other of the first blood filter and the second blood filter.

12. The hemo(dia)filtration apparatus of claim 11, wherein the pump and the balance unit are arranged so that substituate fluid is drawn through the membrane from the dialyzer flow to the blood flow of said other of the first blood filter and the second blood filter to replace fluid removed from the blood flow through the membrane of said one of the first blood filter and the second blood filter.

13. The hemo(dia)filtration apparatus of claim 12, wherein the substituate fluid can be intermittently drawn through the membrane from the dialyzer flow to the blood flow within said one of the first blood filter and the second blood filter to replace fluid removed from the blood flow through the membrane of said other within the first blood filter and the second blood filter.

* * * * *